(12) United States Patent
Benner et al.

(10) Patent No.: US 9,315,842 B2
(45) Date of Patent: Apr. 19, 2016

(54) HELICASE DEPENDENT AMPLIFICATION OF DNA MOLECULES USING NUCLEOTIDE ANALOGS

(71) Applicants: Steven A Benner, Gainesville, FL (US); Zunyi Yang, Gainesville, FL (US)

(72) Inventors: Steven A Benner, Gainesville, FL (US); Zunyi Yang, Gainesville, FL (US)

( * ) Notice: Subject to any disclaimer, the term of this patent is extended or adjusted under 35 U.S.C. 154(b) by 142 days.

(21) Appl. No.: 13/970,111

(22) Filed: Aug. 19, 2013

(65) Prior Publication Data
US 2015/0050695 A1 Feb. 19, 2015

(51) Int. Cl.
C12P 19/34 (2006.01)
C12Q 1/68 (2006.01)

(52) U.S. Cl.
CPC .............. *C12P 19/34* (2013.01); *C12Q 1/6853* (2013.01)

(58) Field of Classification Search
CPC .............................. C12P 19/34; C12Q 1/6853
USPC ........................................ 435/6.1, 6.12, 91.1
See application file for complete search history.

(56) References Cited

U.S. PATENT DOCUMENTS

| 5,049,490 A | 9/1991 | Sutherland |
|---|---|---|
| 6,414,133 B1 | 7/2002 | Dietz-Band |
| 2007/0254304 A1* | 11/2007 | Kong et al. ................. 435/6 |

FOREIGN PATENT DOCUMENTS

| WO | WO 2010/021702 | * | 2/2010 |
|---|---|---|---|
| WO | WO 2010021702 A9 | | 5/2010 |

OTHER PUBLICATIONS

Yang et al. (Analytical Chemistry 2013, vol. 85, No. 9 pp. 4705-4712).*
Yang, Z. Conversion strategy using an expanded genetic alphabet to assay nucleic acids Anal Chem 85 4705-4712, 2013.
Yang, A. Helicase dependent isothermal amplification of DNA and RNA using self-avoiding molecular recognition systems ChemBioChem 16 1365-1370, 2015.
Sharma, N. Recombinase-based isothermal amplification of nucleic acids with self-avoiding molecular recognition systems (SAMRS) ChemBioChem 15 2268-2274, 2014.
Briguglio, I.Inhibition of RNA helicases of ssRNA+ virus belonging to Flaviviridae, Coronaviridae and Picornaviridae families. Int. J. Med. Chem. 2011 Article ID 213135.
Vincent, M. Helicase-dependent isothermal DNA amplification EMBO 5, 8 795-800, 2004.
Lemieux, B. Near instrument-free simple molecular device for rapid detection of herpes simplex viruses Expert Rev Mol Diag 12, 437-443, 2012.

* cited by examiner

*Primary Examiner* — Jezia Riley

(57) ABSTRACT

This invention covers processes for the isothermal amplification of DNA molecules having a preselected sequence. It is based on the unexpected discovery that primers having, at some positions, adenine substituted by 2-aminopurine or diaminopurine, guanine by inosine, thymine by 2-thiothymine, and cytosine by N4-ethylcytosine ("SAMRS nucleotides") were accepted by enzymes used in the standard helicase-dependent amplification (HDA). Further unexpected was the discovery that target nucleotides are efficiently amplified in an HDA-like process (hereinafter abbreviated as simply HDA) using substituted primers. Also discovered was the diminution of spurious products through the use of SAMRS-substituted primers.

8 Claims, 8 Drawing Sheets

Figure 1:
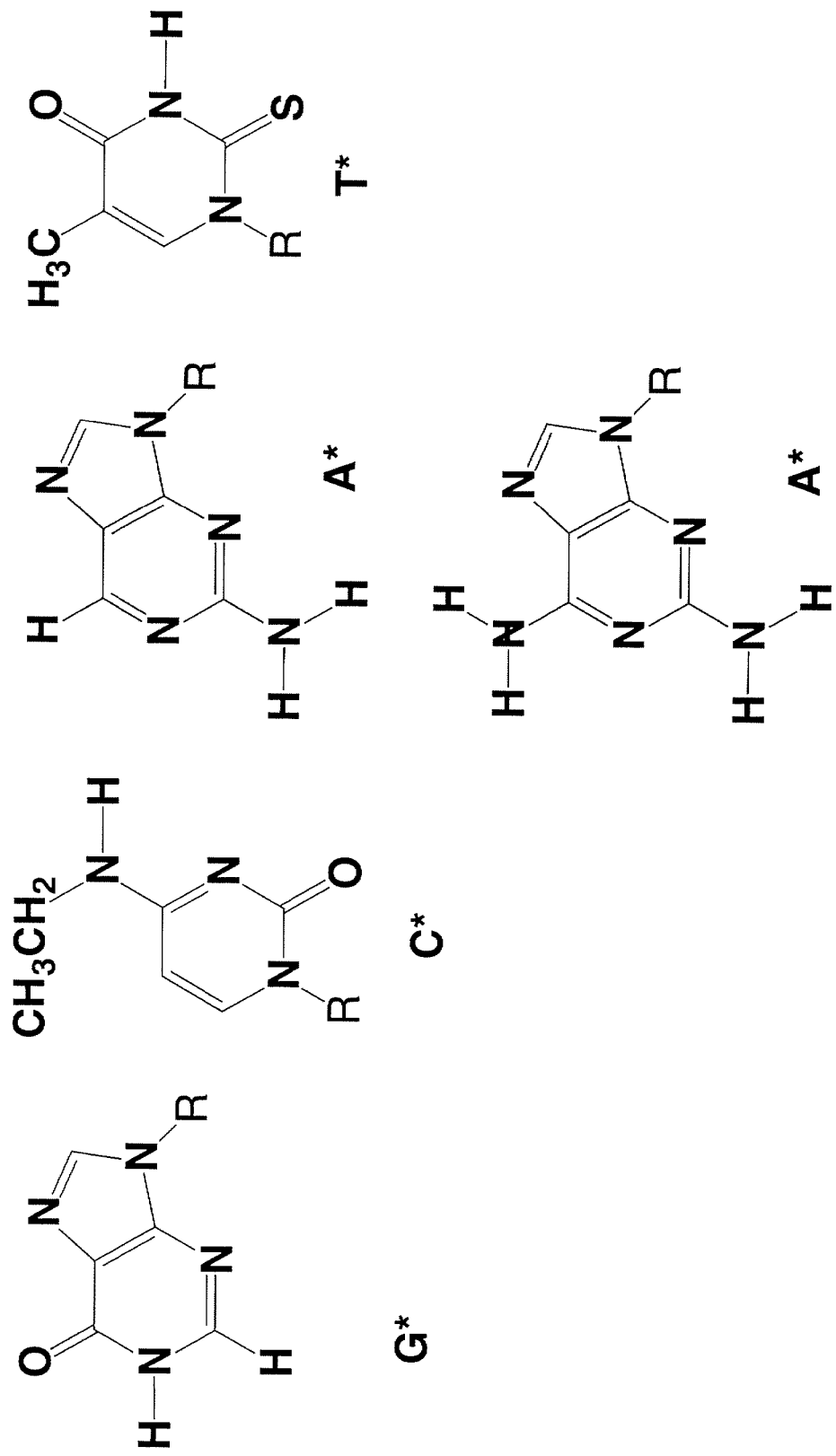

X = N or CH   R = electron withdrawing group

SEQUENCE LISTING

<160> NUMBER OF SEQ ID NOS: 16

<210> SEQ ID NO 1
<211> LENGTH: 25
<212> TYPE: DNA
<213> ORGANISM: Artificial Sequence
<220> FEATURE:
<223> OTHER INFORMATION: Synthetic

<400> SEQUENCE: 1
agatttgtga ttttggtcta gccag          25

<210> SEQ ID NO 2
<211> LENGTH: 25
<212> TYPE: DNA
<213> ORGANISM: Artificial Sequence
<220> FEATURE:
<223> OTHER INFORMATION: Synthetic

<400> SEQUENCE: 2
tgtcaagcag agaatgggta ctcac          25

```
<210> SEQ ID NO 3
<211> LENGTH: 25
<212> TYPE: DNA
<213> ORGANISM: Artificial Sequence
<220> FEATURE:
<223> OTHER INFORMATION: Synthetic

<400> SEQUENCE: 3
agatttgtga ttttggtcta gccag                                          25

<210> SEQ ID NO 4
<211> LENGTH: 25
<212> TYPE: DNA
<213> ORGANISM: Artificial Sequence
<220> FEATURE:
<223> OTHER INFORMATION: Synthetic

<400> SEQUENCE: 4
tgtcaagcag agaatgggta ctcac                                          25

<210> SEQ ID NO 5
<211> LENGTH: 29
<212> TYPE: DNA
<213> ORGANISM: Artificial Sequence
<220> FEATURE:
<223> OTHER INFORMATION: Synthetic

<400> SEQUENCE: 5
acaaagattt gtgattttgg tctagccag                                      29

<210> SEQ ID NO 6
<211> LENGTH: 29
<212> TYPE: DNA
<213> ORGANISM: Artificial Sequence
<220> FEATURE:
<223> OTHER INFORMATION: Synthetic

<400> SEQUENCE: 6
ggactgtcaa gcagagaatg ggtactcac                                      29

<210> SEQ ID NO 7
<211> LENGTH: 29
<212> TYPE: DNA
<213> ORGANISM: Artificial Sequence
<220> FEATURE:
<223> OTHER INFORMATION: Synthetic

<400> SEQUENCE: 7
acaaagattt gtgattttgg tctagccag                                      29

<210> SEQ ID NO 8
<211> LENGTH: 29
<212> TYPE: DNA
<213> ORGANISM: Artificial Sequence
<220> FEATURE:
<223> OTHER INFORMATION: Synthetic

<400> SEQUENCE: 8
ggactgtcaa gcagagaatg ggtactcac                                      29

<210> SEQ ID NO 9
<211> LENGTH: 25
<212> TYPE: DNA
<213> ORGANISM: Artificial Sequence
<220> FEATURE:
<223> OTHER INFORMATION: Synthetic
```

```
<400> SEQUENCE: 9
agatttgtga ttttggtcta gccag                                            25

<210> SEQ ID NO 10
<211> LENGTH: 25
<212> TYPE: DNA
<213> ORGANISM: Artificial Sequence
<220> FEATURE:
<223> OTHER INFORMATION: Synthetic

<400> SEQUENCE: 10
tgtcaagcag agaatgggta ctcac                                            25

<210> SEQ ID NO 11
<211> LENGTH: 29
<212> TYPE: DNA
<213> ORGANISM: Artificial Sequence
<220> FEATURE:
<223> OTHER INFORMATION: Synthetic

<400> SEQUENCE: 11
acaaagattt gtgattttgg tctagccag                                        29

<210> SEQ ID NO 12
<211> LENGTH: 29
<212> TYPE: DNA
<213> ORGANISM: Artificial Sequence
<220> FEATURE:
<223> OTHER INFORMATION: Synthetic

<400> SEQUENCE: 12
ggactgtcaa gcagagaatg ggtactcac                                        29

<210> SEQ ID NO 13
<211> LENGTH: 30
<212> TYPE: DNA
<213> ORGANISM: Artificial Sequence
<220> FEATURE:
<223> OTHER INFORMATION: Synthetic

<400> SEQUENCE: 13
aaacaccatg ctaaacacag tgggggaca                                        30

<210> SEQ ID NO 14
<211> LENGTH: 31
<212> TYPE: DNA
<213> ORGANISM: Artificial Sequence
<220> FEATURE:
<223> OTHER INFORMATION: Synthetic

<400> SEQUENCE: 14
atctatccca ttctgcagct tcctcattga t                                     31

<210> SEQ ID NO 15
<211> LENGTH: 30
<212> TYPE: DNA
<213> ORGANISM: Artificial Sequence
<220> FEATURE:
<223> OTHER INFORMATION: Synthetic

<400> SEQUENCE: 15
aaacaccatg ctaaacacag tgggggaca                                        30

<210> SEQ ID NO 16
<211> LENGTH: 31
```

```
<212> TYPE: DNA
<213> ORGANISM: Artificial Sequence
<220> FEATURE:
<223> OTHER INFORMATION: Synthetic

<400> SEQUENCE: 16
atctatccca ttctgcagct tcctcattga t                                    31
```

HELICASE DEPENDENT AMPLIFICATION OF DNA MOLECULES USING NUCLEOTIDE ANALOGS

STATEMENT REGARDING FEDERALLY SPONSORED RESEARCH OR DEVELOPMENT

This invention was made with government support under a grant awarded by the United States Defense Advanced Research Project Agency (R0011-11-2-0018). The government has certain rights in the invention.

CROSS REFERENCE TO RELATED APPLICATIONS

None

THE NAMES OF THE PARTIES TO A JOINT RESEARCH AGREEMENT

Not applicable

INCORPORATION-BY-REFERENCE OF MATERIAL SUBMITTED ON A COMPACT DISC

None

BACKGROUND OF THE INVENTION (1) Field of the Invention

The field of this invention is nucleic acid chemistry, more specifically the field that covers methods for increasing the number of DNA molecules that have a preselected target sequence ("amplifying" that target sequence), and most specifically the field that covers amplification procedures that are done isothermally, without the temperature cycling used in the classical polymerase chain reaction.

(2) Description of Related Art

For practical applications in many areas, including diagnostic procedures that target DNA- and RNA-molecules in biological samples, methods are desired that "amplify" specific nucleic acid sequences. Classically, this has been done by the polymerase chain reaction (PCR) [R. K. Saiki, D. H. Gelfand, S. Stoffel, S. J. Scharf, R. Higuchi, G. T. Horn, K. B. Mullis, H. A. Erlich (1988) Primer-directed enzymatic amplification of DNA with a thermostable DNA polymerase. Science 239, 487-491]. Here, a "forward primer" that binds to a pre-selected target oligonucleotide is annealed to the target sequence to form a duplex. Then, the primer is incubated with a DNA polymerase and the appropriate 2'-deoxynucleoside triphosphates to yield a product that is complementary (in the Watson-Crick sense) to the target oligonucleotides; the target and its complement, as it is formed, are bound in a double stranded double helix. The double strand is then "melted" by heating, typically to temperatures above 75° C., yielding the two complementary DNA strands as single strands. Each strand is freed by heating from its complement. The original target is then able to bind to a second forward primer, while the product DNA molecule is able to bind to a "reverse primer", which is designed to bind to a preselected site downstream in the product DNA molecule. The polymerase extension is then repeated, with both primers extended to give full-length products, again as duplexes (now two in number). The two strands are then separated by heating to allow more forward and reverse primer to anneal, and the cycle is repeated. The results are multiple copies of both the target DNA molecule and its complement. In asymmetric PCR, the ratio of these two is different from unity.

Classical PCR is widely used throughout research, science, and technology, being the method of choice to detect small amounts of DNA in complex biological samples. Nevertheless, the use of temperature cycling to separate the two strands in product duplexes is undesirable in many applications, including applications that want to amplify target DNA at points-of-care, in doctors offices, and in the field. The desire to amplify target DNA molecules without needing to do repeated temperature cycling is indicated by the literature that searches for amplification methods that do not need temperature cycling, including those known as "recombinase polymerase amplification" (RPA) [Piepenburg, O., Williams, C. H., Stemple, D. L., Armes, N. A. (2006) DNA Detection using recombination proteins. *PLoS Biol* 4 (7): e204], rolling circle amplification (RCA), NASBA, helicase-dependent amplification (HDA) [Tong, Y., Lemieux, B.,; Kong, H. (2011) Multiple strategies to improve sensitivity, speed and robustness of isothermal nucleic acid amplification for rapid pathogen detection. *BMC Biotechnol.* 11 Art. No: 50] [Lemieux, B., Li, Y.; Kong, H. M., Tang, Y. W. (2012) Near instrument-free, simple molecular device for rapid detection of herpes simplex viruses: *Expert Review Molec. Diagnostics* 12, 437-443 DOI: 10.1586/ERM.12.34] and LAMP, among others. These are called "isothermal amplification" methods.

Isothermal amplification methods frequently do not perform well, however. In many cases, the extent of amplification appears to depend on the specific sequence being amplified or (perhaps) the sequence of probes and/or primers used in the amplification. In some cases, the amplification fails entirely. In many cases, extra "spurious" products are observed to arise in addition to the target amplicon. Spurious products are especially seen when isothermal amplification is attempted for more than one target nucleic acid in a single sample ("multiplexing").

Essentially no theory explains these and other variable results, although speculation can be found in the public and private art, some of it contradictory, other explanations being informal. Without any attempt to be exhaustive, speculative suggestions include the possibility that at low temperatures, non-Watson Crick interactions might cause some of the DNA molecules involved (primer, probe, or analyte) to fold in a way that defeats the amplification process. Others have suggested that high temperatures must be regularly traversed to avoid an (often unknown) intra- or intermolecular interaction from capturing the system as an artifact. Primer-primer interactions have been invoked to explain failure of various isothermal amplification systems, especially when is multiplexing is attempted.

None of these explanations are established. Few data allow us to prefer one over another. As a consequence, the art contains no clear guidance as to what experiments might be tried to overcome these problems, and to generate reliable procedures of performing isothermal amplification for all target sequences and, especially, for multiple (more than one) target sequences.

This is especially true for the isothermal amplification method known as helicase-dependent amplification (HDA). Instead of raising the temperature to separate product duplexes, HDA uses a protein known as helicase. In theory, helicase pulls two strands apart to allow primers to bind to create two duplexes from an original single duplex. While HDA creates successful amplification for many targets, it unfortunately does not for most targets. Again, additional products are often seen with HDA targeting single DNA molecules, often causing the isothermal amplification to fail.

Attempts to multiple HDA nearly always fail. Again, while the spurious products are occasionally called "primer dimers", few if any examples exist where those structures are proven. In any case, formation of these spurious products limits sensitivity and multiplexing. Further, standard HDA cannot use primer concentrations higher than ca. 0.2 µM which limit the speed of detection.

BRIEF SUMMARY OF THE INVENTION

This invention is based on the unexpected discovery that primers ("substituted primers") in which at least some of the A, T, G, and C nucleobases are substituted at some (but not all) sites (positions) with analogs designated A*, T*, G* and C*, are accepted by enzymes that work together with helicase to effect HDA-like amplification. The presently preferred substitutions replace adenine by 2-aminopurine or diaminopurine (either is defined as A*), replace guanine by inosine (defined as G*), replace thymine by 2-thiothymine (defined as T*), and replace cytosine by N4-ethylcytosine (defined as C*). This invention is further based on the unexpected discovery that target nucleotides are indeed amplified in an HDA-like process (hereinafter abbreviated as simply HDA) using these substituted primers. Further, this invention is based on the discovery that HDA-like processes where its substituted primers are tagged with oligonucleotides incorporating nucleotides selected from as artificially expanded genetic information system (AEGIS, herein defined) also perform well.

BRIEF DESCRIPTION OF THE SEVERAL VIEWS OF THE DRAWING(S)

FIG. 1. The presently preferred nucleobases analogs that substitute for G, C, A, and T in the substituted primers, where R is the point of attachment to the oligonucleotide.

Figure 2:
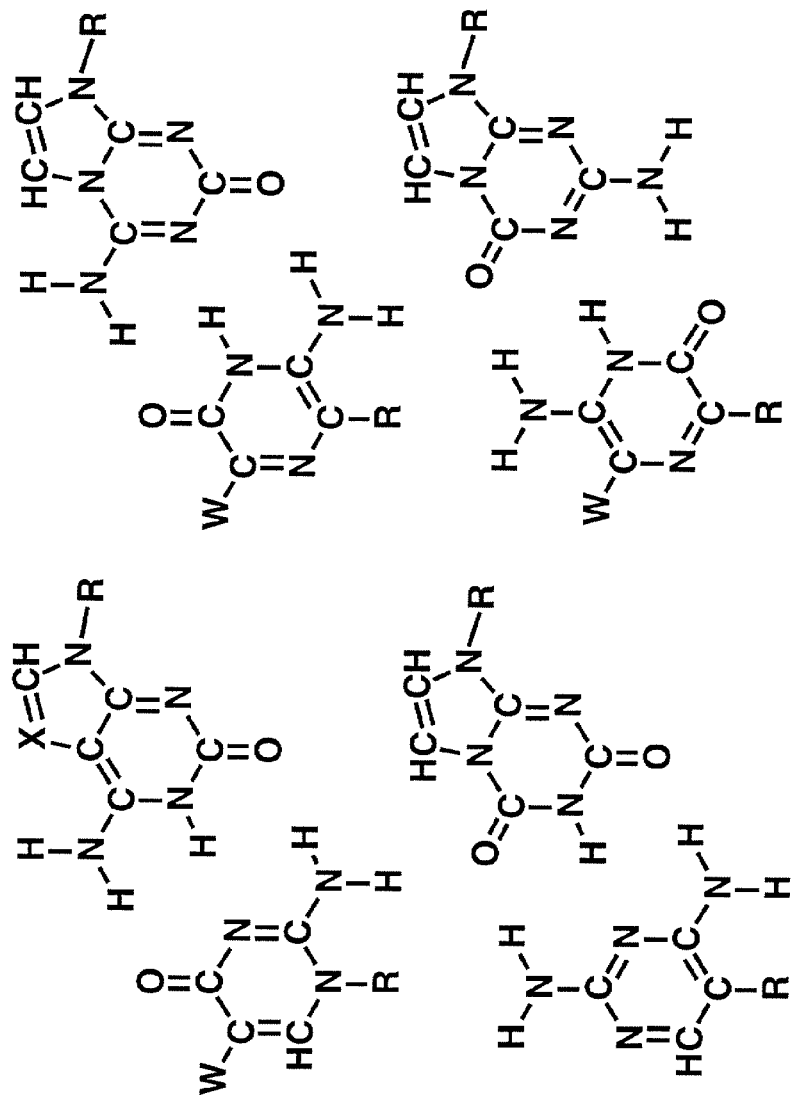

FIG. 2. The presently preferred components selected from an artificially expanded genetic information system, where R is the point of attachment to the oligonucleotide, and W is an electron withdrawing group such as nitro or cyano.

Figure 3:
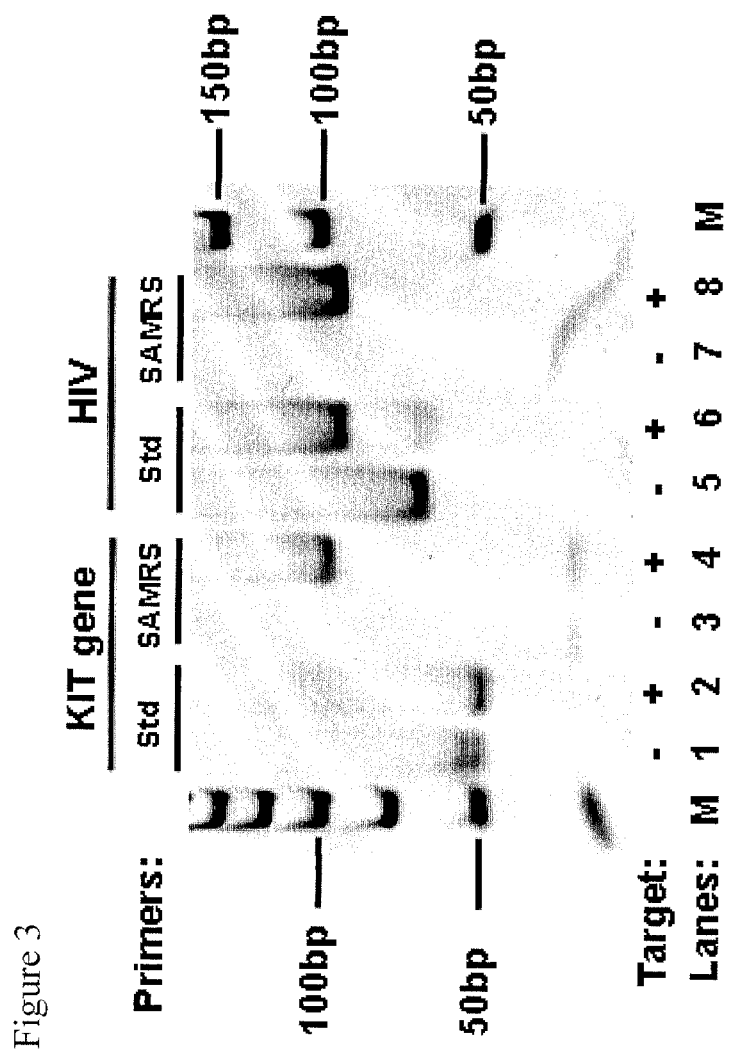

FIG. 3. (Lane 1 and 2): Standard primers (Std) generate spurious products, perhaps primer-dimers, both with the KIT gene (the preselected target, lane 1, −) absent, and with KIT gene present (lane 2, +); (Lane 3 and 4): SAMRS primers of the instant invention generate product with KIT gene (lane 4, +), and no spurious products without the KIT gene target (lane 3, −); (Lane 5 and 6): Standard primers (Std) generate spurious product without HIV target (lane 5, −) or some spurious product and product with HIV target (lane 6, +); (Lane 7 and 8): SAMRS primers generate product with HIV target (lane 8, +), and no spurious products without HIV target (lane 7, −).

Figure 4:
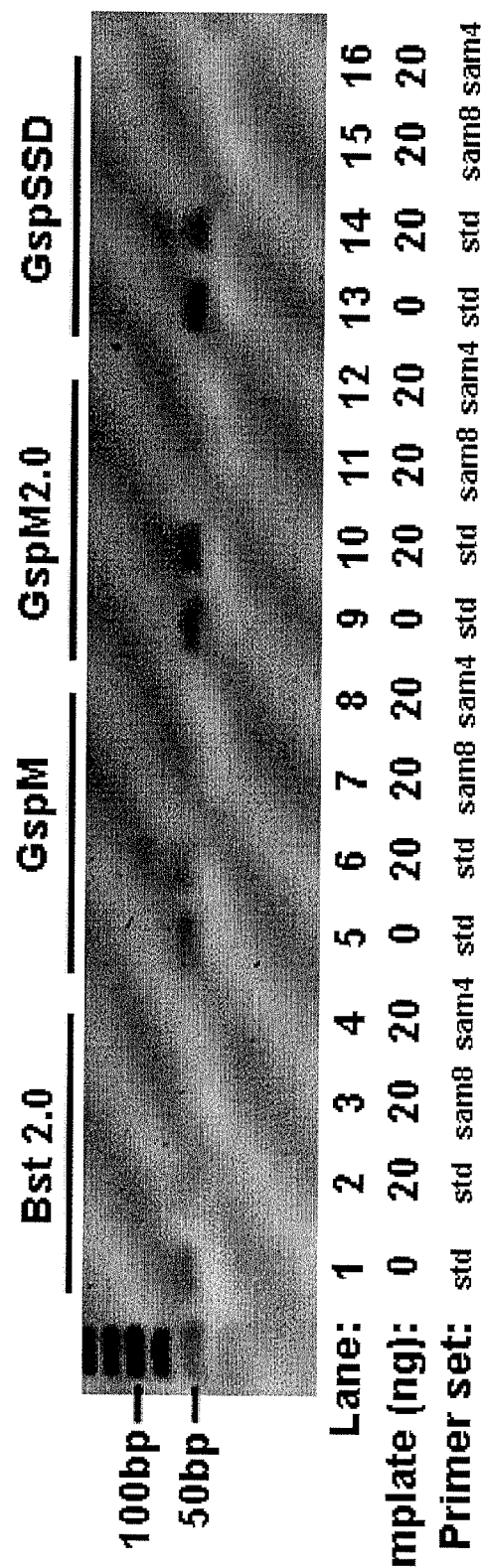

FIG. 4. Data from Example 1. (Lanes 1 and 2): Bst2.0 with IsoAmpIII (BioHelix, Beverly Mass., 2 µL each) with 0 ng or 20 ng (respectively) of target with KIT primers with all sites in the primers containing standard (Std) nucleotides. (Lane 3): Bst2.0 with IsoAmpIII (2 µL each) with 20 ng of target with SAMRS8 primers containing eight SAMRS nucleotides in the substituted primers. (Lane 4): Bst2.0+IsoAmpIII (2 µL each) with 20 ng of target with SAMRS4 primers occupied by four SAMRS nucleotides in the substituted primers. (Lanes 5 and 6): GspM and IsoAmpIII (2 µL each) with 0 ng or 20 ng (respectively) of target with KIT primers with all sites occupied by standard (Std) nucleotides. (Lane 7): GspM+IsoAmpIII (2 µL each) with 20 ng of target with SAMRS8 primers containing eight SAMRS nucleotides in the indicated positions primers. (Lane 8): GspM and IsoAmpIII (2 µL each) with 20 ng of target with SAMRS4 primers containing four SAMRS nucleotides in the substituted primers. (Lane 9 and 10): GspM2.0 and IsoAmpIII (2 µL each) with 0 ng or 20 ng of target with std KIT primers. (Lane 11): GspM2.0 and IsoAmpIII (2 µL each) with 20 ng of target with SAMRS8 primers containing eight SAMRS nucleotides in the indicated positions. (Lane 12): GspM2.0 and IsoAmpIII (2 µL each) with 20 ng of target with SAMRS4 primers containing four SAMRS nucleotides in the indicated positions. (Lanes 13 and 14): GspSSD and IsoAmpIII (2 µL each) with 0 ng or 20 ng of target with KIT primers with all sites occupied by standard (Std) nucleotides. (Lane 15): GspSSD and IsoAmpIII (2 µL each) with 20 ng of target with SAMRS8 primers containing eight SAMRS nucleotides in the indicated positions. (Lane 16): GspSSD and IsoAmpIII (2 µL each) with 20 ng of target with SAMRS4 primers containing four SAMRS nucleotides in the indicated positions.

Figure 5:
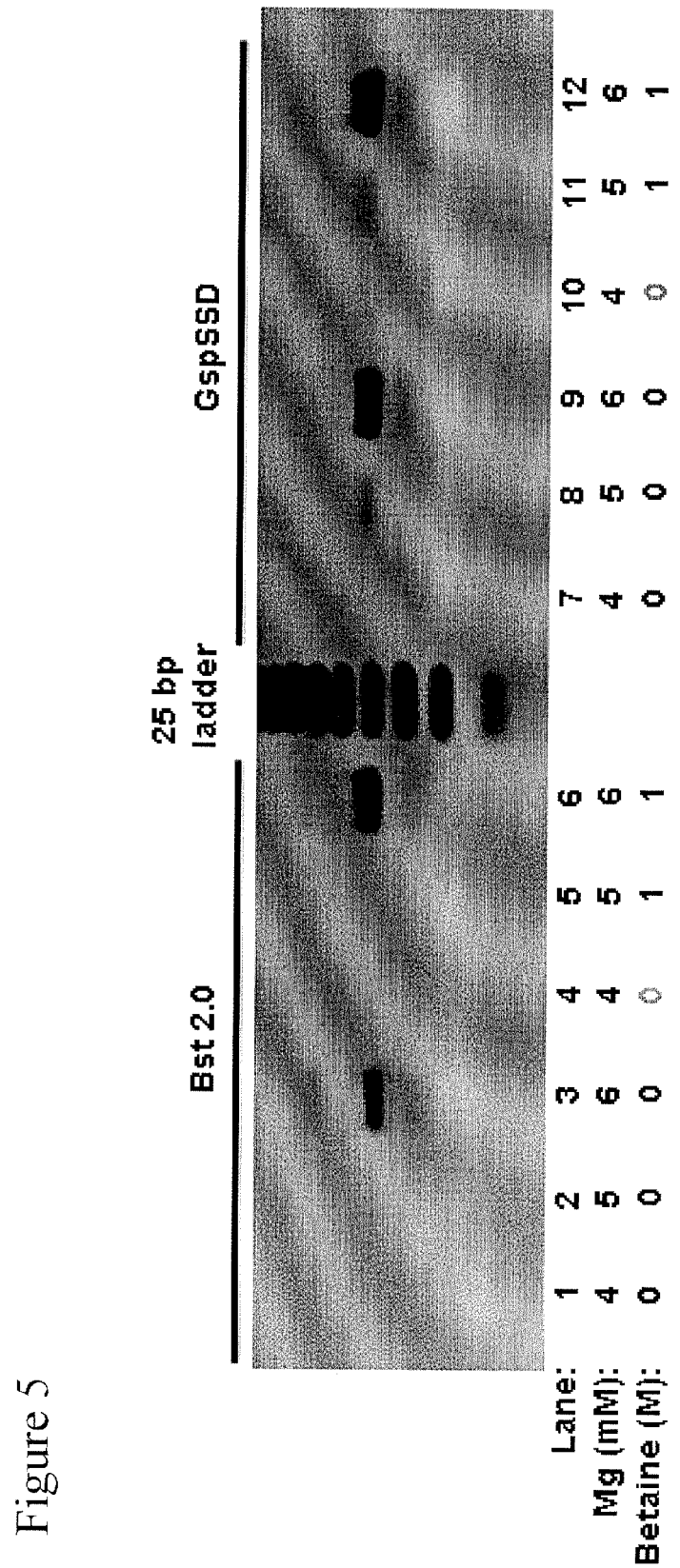

FIG. 5. Data from Example 2. (Lanes 1, 2 and 3): Bst2.0+IsoAmpIII (2 µL each), 20 ng of target and 4, 5 or 6 mM $MgSO_4$ (respectively). (Lane 4, 5 and 6): Bst2.0 and IsoAmpIII (2 µL each), 20 ng of target and 4, 5 or 6 mM $MgSO_4$ plus 1 M betaine. (Lanes 7, 8 and 9): GspSSD and IsoAmpIII (2 µL each), 20 ng of target and 4, 5 or 6 mM $MgSO_4$. (Lanes 10, 11 and 12): GspSSD and IsoAmpIII (2 µL each), 20 ng of target and 4, 5 or 6 mM $MgSO_4$ plus 1 M betaine.

Figure 6:
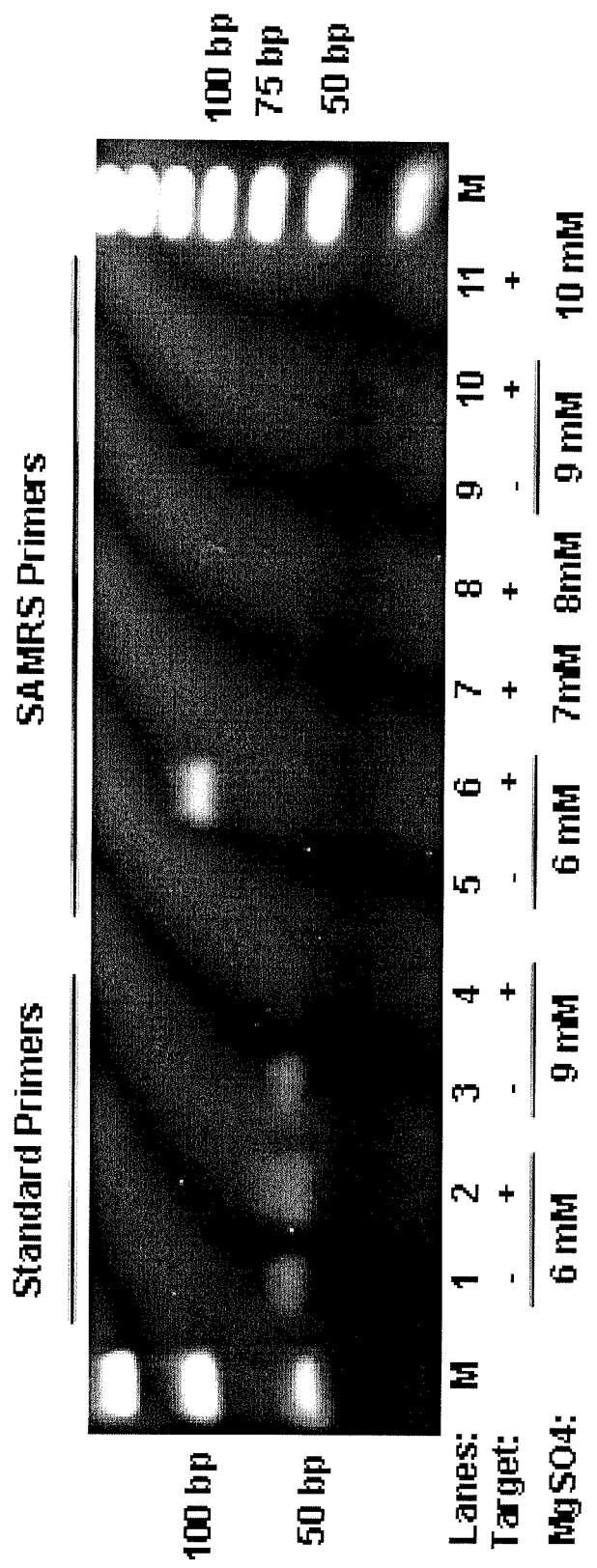

FIG. 6. Data from Example 3. M lanes are markers, DNA ladders separated by 50 bp (left) and 25 bp (right). (Lanes 1, 2, 3, and 4): KIT-Standard primers containing no SAMRS-components. (Lanes 5, 6, 7, 8, 9, 10, and 11): KIT-SAMRS primers, having SAMRS nucleotides at the indicated positions. The target was human genomic DNA (male, 20 ng/reaction), with target (+) or without target (−), the latter being a negative control. The final $MgSO_4$ concentration in each reaction was, in various lanes, 6 mM, 7 mM, 8 mM, 9 mM, and 10 mM.

Figure 7:
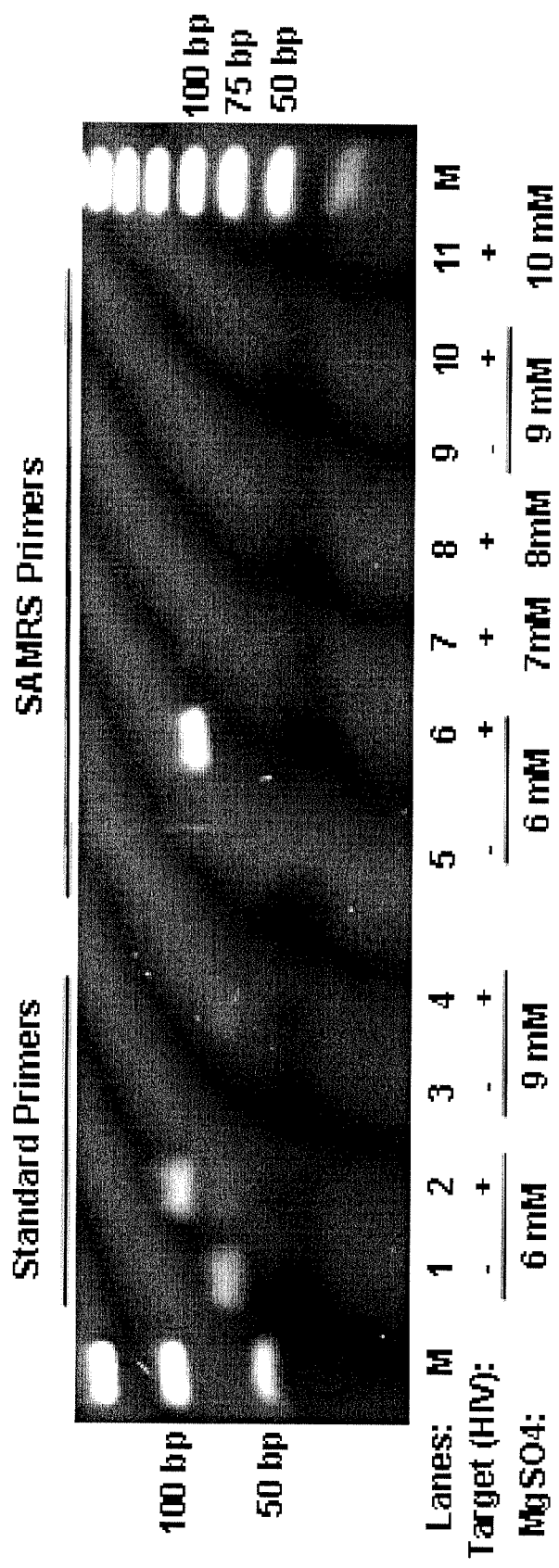

FIG. 7. Data from Example 4. M lanes are markers, DNA ladders separated by 50 bp (left) and 25 bp (right). (Lanes 1, 2, 3, and 4): HIV targets with attempted amplification using standard primers. (Lanes 5, 6, 7, 8, 9, 10, and 11): HIV SAMRS primers. The target was a synthetic HIV-DNA-96mer (0.2 fmole/reaction), with HIV target (+) or without HIV target (−); The final $MgSO_4$ concentration in each reaction was, in various lanes, 6 mM, 7 mM, 8 mM, 9 mM, and 10 mM.

Figure 8:
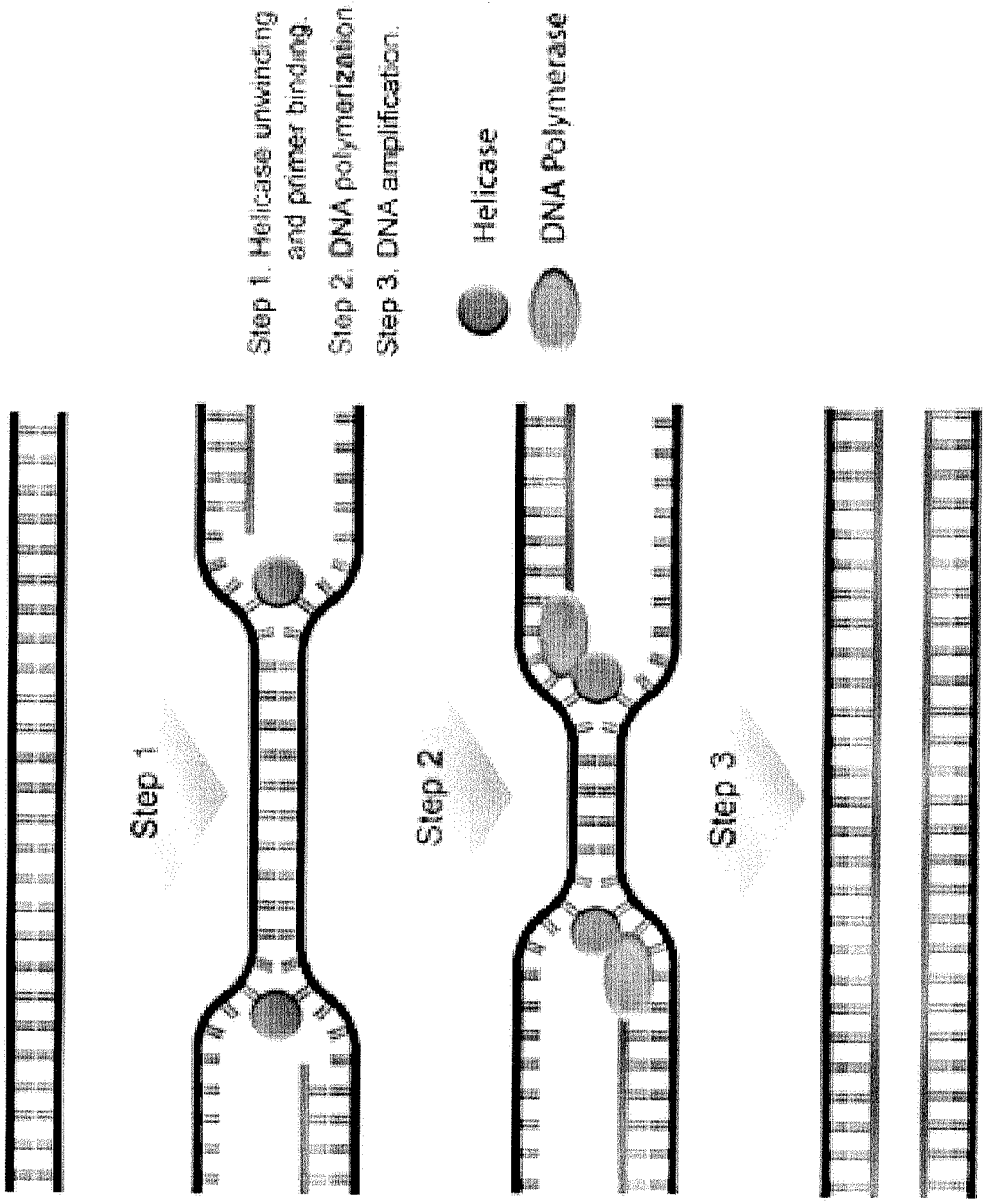

FIG. 8. Schematic showing the mechanism for helicase-dependent amplification (HAD) reactions. Step 1 is helicase unwinding and primer binding. Step 2 is DNA polymerization. Step 3 is DNA amplification. The round circles are helicase molecules. The ellipses are molecules of DNA polymerases.

DETAILED DESCRIPTION OF THE INVENTION

1. Narrative

The key inventive feature of this invention are forward and reverse primers where some of their A, T, G, and C nucleobases are substituted at some sites (positions) with analogs designated (respectively) A*, T*, G* and C* ("SAMRS" nucleotides). As is standard in the art, and for both classical and isothermal PCR, the first step in primer design is to select the part, or segment, or sequence of a DNA molecule, for which amplification is sought. The sequence of the forward primers is then selected so that the forward primer is complementary to a part, or segment, of the target sequence, 3'-adjacent to the part of the target that is to be copied. As is also standard in the art, the reverse primer is complementary to a segment "downstream" on the product after the forward primer is extended by template-directed polymerization. As is standard in the art, the forward and reverse primers are designed to give a reasonably sized amplicon product.

References describing the design of sequences of primers to implement classical HDA can be found in the following literature, and references cited therein, which are incorporated in their entirety by citation [Tong, Y., Lemieux, B.,; Kong, H. (2011) Multiple strategies to improve sensitivity, speed and robustness of isothermal nucleic acid amplification for rapid pathogen detection. *BMC Biotechnol.* 11 Art. No: 50] [Lemieux, B., Li, Y.; Kong, H. M., Tang, Y. W. (2012) Near instrument-free, simple molecular device for rapid detection of herpes simplex viruses: *Expert Review Molec. Diagnostics* 12, 437-443 DOI: 10.1586/ERM.12.34].

After the primers are chosen to produce the desired amplicon, some of the standard nucleotides in the primer must be substituted by their corresponding SAMRS nucleotide analog. This specification and its examples teach that not all sites should be substituted. Rather, this specification and its examples teach that preferably not fewer than two, and preferably not more than six, substitutions should be made. The presently preferred number of substitutions is four.

Presently preferred are substitutions near the 3'-end of the primer, most preferably at sites n−1, n−2, n−3 . . . , where n is the last, 3'-site in the primer. If the number of SAMRS nucleotides is four, then these are preferably placed at present at sites n−1, n−2, n−3, and n−4, where site n is the 3'-terminal (last) site in the oligonucleotides primer. The presently preferred n substitutions are within the 3'-terminal n+1 sites, the 3'-terminal seven sites for the maximum substitutions (6) and the 3'-terminal three sites for the minimum number of preferred substitutions (2), and the 3'-terminal five sites for most preferred number of substitutions (4).

The presently preferred SAMRS nucleotides replace adenine (A) in the primer by 2-aminopurine or diaminopurine (either is defined as A*), replace guanine (G) in the primer by inosine (defined as G*), replace thymine (T) in the primer by 2-thiothymine (defined as T*), and replace cytosine (C) in the primer by N4-ethylcytosine (defined as C*). Protected phosphoramidites suitable for solid phase DNA synthesis of these nucleoside analogs are well known in the art.

After they are designed, the SAMRS-containing primers are synthesized by solid phase automated synthesis from the corresponding protected phosphoramidites. The methods for synthesizing such primers are described in the following two references, which are incorporated in their entirety herein.

[Hoshika, S., Leal, N., Chen, F., Benner, S. A. (2010) Artificial genetic systems. Self-avoiding DNA in PCR and multiplexed PCR. *Angew. Chem. Int. Edit.* 49, 5554-5557]

[Yang, Z., Chen, F., Alvarado, J. B., Benner, S. A. (2011) Amplification, mutation, and sequencing of a six-letter synthetic genetic system. *J. Am. Chem. Soc.* 133, 15105-15112]

Once the primers are prepared, in many of its respects, the isothermal amplification process of the instant invention proceeds just as standard HDA [Tong, Y., Lemieux, B., Kong, H. (2011) Multiple strategies to improve sensitivity, speed and robustness of isothermal nucleic acid amplification for rapid pathogen detection. *BMC Biotechnol.* 11 Art. No: 50] [Lemieux, B., Li, Y.; Kong, H. M., Tang, Y. W. (2012) Near instrument-free, simple molecular device for rapid detection of herpes simplex viruses: *Expert Review Molec. Diagnostics* 12, 437-443 DOI: 10.1586/ERM.12.34]. For this reason, the assays are called "HDA-like". In particular, the invention with its inventive substituted SAMRS primers may be practiced using the helicase enzymes and triphosphates contained in the IsoAmp™ kits sold by BioHelix (Beverly, Mass.) for standard HDA. However, as disclosed in the examples, certain polymerases proved to be exceptionally well suited for the instant invention. Further, optionally, the assay of the instant invention may include single stranded binding protein.

2. Examples

EXAMPLE 1

Example 1 describes the amplification of a target DNA molecule (the KIT gene) presented within human genomic DNA (20 ng, corresponding to ca. 6000 copies). This example demonstrated the surprising ability of helicase in conjunction with various polymerases to amplify targets with high efficiency and low noise, even when SAMRS-containing primers were used. It also provided the experimental evidence for the presently preferred use of primers containing four SAMRS nucleotides (G*, C*, T*, and A*), not eight SAMRS nucleotides in the HDA-like process. This example also demonstrated that SAMRS-substituted primers work in this HDA-like assay with different Gsp DNA polymerases (Bst2.0, GspM, Gspm2.0, and GspSSD, all from OptiGene), These experiments further showed that:

1) Standard primers gave more spurious products (hypothetically "primer dimers") than desired amplicon product for all polymerases tested.

2) Primers containing four SAMRS components produced the desired amplicon, but no spurious products with GspM and Gspm2.0 DNA polymerases. Primers containing eight SAMRS components did not produce either "primer dimer" or desired amplicon product, regardless of which polymerase was used.

3) Primers containing four SAMRS components produced only trace amounts of product when the GspSSD DNA polymerase was used. Therefore, the GspM and Gspm2.0 DNA polymerases are preferred.

The SAMRS-containing primers used in this study are shown below. The bold underlined segments indicate SAMRS substitution, with A* as 2-aminopurine; T* as 2-thio-T; G* as inosine; and C* as N-ethyl-dC.

```
KIT-90-F-25mer-std:
                                      SEQ ID NO. 1
5'-AGATTTGTGATTTTGGTCTAGCCAG-3'

KIT-90-R-25mer-std:
                                      SEQ ID NO. 2
5'-TGTCAAGCAGAGAATGGGTACTCAC-3'

KIT-90-F-25mer:
                                      SEQ ID NO. 3
5'-AGATTTGTGATTTTGGTCTAGCCAG-3'

KIT-90-R-25mer:
                                      SEQ ID NO. 4
5'-TGTCAAGCAGAGAATGGGTACTCAC-3'

KIT-98-F-29mer:
                                      SEQ ID NO. 5
5'-acaaAGATTTGTGATTTTGGTCTAGCCAG-3'

KIT-98-R-29mer:
                                      SEQ ID NO. 6
5'-ggacTGTCAAGCAGAGAATGGGTACTCAC-3'
```

These primers were mixed at room temperature with 20 ng of human genomic DNA containing the target DNA sequence as a segment in buffered aqueous solution with a helicase and other components in the IsoAmp mixture from BioHelix (Beverly Mass.), a DNA polymerase from those listed in Table 1, the 2'-deoxynucleoside triphosphates, and various other components listed in Table 1. The mixture was then incubated at 65° C. for 90 min. The conditions are as shown below:

TABLE 1

| Components | KIT Std primers | KIT-SAMRS8-25mer Primers | KIT-SAMRS4-29mer Primers | No Template Control | Final Conc. |
|---|---|---|---|---|---|
| dH$_2$O in primer mix | 10.5 μL | 10.5 μL | 10.5 μL | 10.5 μL | 25 μL |
| KIT-F-std (5 μM) | 1 μL | | | 1 μL | 0.2 μM |
| KIT-R-std (5 μM) | | | | | 0.2 μM |
| KIT-F-25mer-SMS (5 μM) | | 1 μL | | 1 μL | 0.2 μM |
| KIT-R-25mer-SMS (5 μM) | | | | | 0.2 μM |
| KIT-F-29mer-SMS (5 μM) | | | 1 μL | 1 μL | 0.2 μM |
| KIT-R-29mer-SMS (5 μM) | | | | | 0.2 μM |
| dH$_2$O not in master mix | | | | 2 μL | |
| Genomic DNA (10 ng/μL) | 2 μL | 2 μL | 2 μL | | 20 ng/25 μL |
| IsoAmp dNTP Solution | 2 μL | 2 μL | 2 μL | 2 μL | 1.14× |
| NaCl (500 mM) | 2 μL | 2 μL | 2 μL | 2 μL | 40 mM |
| MgSO$_4$ (100 mM) | 1 μL | 1 μL | 1 μL | 1 μL | 4 mM |
| 10× Annealing Buffer II | 2.5 μL | 2.5 μL | 2.5 μL | 2.5 μL | 1× |
| IsoAmp Enzyme Mix III (BioHelix) | 2 μL | 2 μL | 2 μL | 2 μL | 2× |
| Bst 2.0 (NEB) [8 U/μL] | 2 μL | 2 μL | 2 μL | 2 μL | 0.64 U/μL |
| GspM (OptiGene, 8 U/μL) | 2 μL | 2 μL | 2 μL | 2 μL | 0.64 U/μL |
| GspM 2.0 (OptiGene, 8 U/μL) | 2 μL | 2 μL | 2 μL | 2 μL | 0.64 U/μL |
| GspSSD (OptiGene, 8 U/μL) | 2 μL | 2 μL | 2 μL | 2 μL | 0.64 U/μL |

After each reaction was incubated at 65° C. for 90 min, sample (10 μL) were diluted with a solution loading dye (4 μL). This was loaded as well known in the art on a 2.5% agarose gel. Electrophoresis was used to resolve the PCR products. The results are shown in FIG. 4.

EXAMPLE 2

Demonstrating the Functioning of SAMRS-substituted Primers in an HDA-like Assay Targeting KIT Gene Using GsSSD and Bst2.0 DNA Polymerases The efficiency of a KIT primer pair with four SAMRS bases (G*, C*, T*, and A*) was demonstrated using helicase-dependent amplification (HDA)-like architectures with Bst2.0 and GspSSD and various concentrations of MgSO$_4$ (4 mM, 5 mM, and 6 mM). These experiments showed that:
1) Increasing the concentration of MgSO$_4$ from 4 mM to 6 mM increased the efficiency by which the desired amplicon was obtained, with both Bst2.0 and GspSSD DNA polymerases.
2) Adding betaine (1 M) increased the efficiency by which the desired amplicon was obtained, and is presently preferred for GC rich targets.

The primers used in this example are shown below. The underlined bold segments are again the sites where the standard nucleotide was substituted by the corresponding SAMRS nucleotide. Thus, the underlined A indicates A* as DAP (2,6-diaminopurine); the underlined T indicates T* as 2-thio-T; the underlined G indicates G* as inosine; the underlined C indicates C* as N-ethyl-dC.

```
KIT-98-F-29mer:
                                        SEQ ID NO. 7
5'-acaaAGATTTGTGATTTTGGTCTAGCCAG-3'

KIT-98-R-29mer:
                                        SEQ ID NO. 8
5'-ggacTGTCAAGCAGAGAATGGGTACTCAC-3'
```

The IsoAmp solution containing polymerases and 2'-deoxynucleoside triphosphates were mixed with the components shown in Table 2 at room temperature. Then, the mixture was incubated at 65° C. for 90 min, sample (10 μL) was diluted with a solution of loading dye (4 μL) and loaded on a 2.5% agarose gel and subjected to electrophoresis to resolve the PCR products. The results are shown in FIG. 5.

TABLE 2

| Components | KIT-SAMRS-29mer Primers | No Template Control | Final Conc. |
|---|---|---|---|
| dH$_2$O in primer mix | 10.5 μL | 10.5 μL | 25 μL |
| KIT-F-29mer-SMS (5 μM) | 1 μL | 1 μL | 0.2 μM |
| KIT-R-29mer-SMS (5 μM) | | | 0.2 μM |
| dH$_2$O not in master mix | | 2 μL | |
| Genomic DNA (10 ng/μL) | 2 μL | 0 μL | 20 ng/25 μL |
| IsoAmp dNTP Solution | 2 μL | 2 μL | 1.14× |
| NaCl (500 mM) | 2 μL | 2 μL | 40 mM |
| MgSO$_4$ (100 mM) | 1 μL or 1.25 μL or 1.5 μL | 1 μL or 1.25 μL or 1.5 μL | 4 mM or 5 mM or 6 mM |
| Betaine (5M) | 5 μL | 5 μL | 1M |
| 10× Annealing Buffer II | 2.5 μL | 2.5 μL | 1× |
| IsoAmp Enzyme Mix III (BioHelix) | 2 μL | 2 μL | 2× |
| Bst 2.0 (NEB) [8 U/μL] | 2 μL | 2 μL | 0.64 U/μL |
| GspSSD (OptiGene, 8 U/μL) | 2 μL | 2 μL | 0.64 U/μL |

EXAMPLE 3

Demonstrating the Functioning of SAMRS-substituted Primers in HDA-like Assays Targeting KIT Genes Using GsSSD DNA Polymerases This example compared the efficiency and specificity of primers substituted with SAMRS nucleotides (containing G*, C*, T*, and A*) with primers containing only standard nucleotides (no SAMRS nucleotides) to amplify the KIT gene as the target double stranded DNA molecule (presented within whole human Genomic DNA) and HIV DNA (HIV-DNA-96mer, presented as a synthetic simulant) using GspSSD under different concentrations of MgSO$_4$ (6 mM, 7 mM, 8 mM, 9 mM, and 10 mM). In summary, these experiments showed that:

1. Increasing the MgSO$_4$ concentrations from 6 mM to 10 mM was shown to decrease the efficiency of HDA-like amplification using SAMRS-substituted primers. Thus, MgSO$_4$ concentrations at 6 mM are presently preferred.

2. SAMRS primers generated product in the presence of targets (genomic DNA or HIV-DNA-96mer) without the formation of any spurious "primer-dimer" when the target is present, and generated no product in the negative control experiment that lacks targets. However, standard primers produced spurious "primer-dimer" products when the target was present and when the target was absent.

Oligonucleotides used in amplifying KIT gene in human genomic DNA are shown below. The underlined bold A indicates A* as 2-aminopurine; the underlined bold T indicates T* as 2-thio-T; the underlined bold G indicates G* as inosine; the underlined bold C indicates C* as N-ethyl-dC. All components (Table 3, primers, substituted or standard, 2'-deoxynucleoside triphosphates, polymerases, and helicase as part of the IsoAmp kit, obtained from BioHelix), were mixed at room temperature. They were then incubated at 65° C. for 90 min.

```
KIT-90-F-25mer-std:
                                SEQ ID NO. 9
5'-AGATTTGTGATTTTGGTCTAGCCAG-3'

KIT-90-R-25mer-std:
                                SEQ ID NO. 10
5'-TGTCAAGCAGAGAATGGGTACTCAC-3'

KIT-98-F-29mer:
                                SEQ ID NO. 11
5'-acaaAGATTTGTGATTTTGGTCTAGCCAG-3'

KIT-98-R-29mer:
                                SEQ ID NO. 12
5'-ggacTGTCAAGCAGAGAATGGGTACTCAC-3'
```

TABLE 3

| Components | KIT-Std-Primers | KIT-SAMRS-Primers | No Template Control | Final Conc. |
|---|---|---|---|---|
| dH$_2$O in primer mix | 9 µL | 9 µL | 9 µL | 25 µL |
| KIT-90-F-25mer-Std (5 µM) | 1 µL | | 1 µL | 0.2 µM |
| KIT-90-R-25mer-Std (5 µM) | | | | 0.2 µM |
| KIT-98-F-29mer-SMS (5 µM) | | 1 µL | 1 µL | 0.2 µM |
| KIT-98-R-29mer-SMS (5 µM) | | | | 0.2 µM |
| dH$_2$O in negative control | | | 2 µL | |
| Human Genomic DNA (10 ng/µL) | 2 µL | 2 µL | | 20 ng/25 µL |
| IsoAmp dNTP Solution | 2 µL | 2 µL | 2 µL | 1.14× |
| NaCl (500 mM) | 2 µL | 2 µL | 2 µL | 40 mM |
| 10× Annealing Buffer II | 2.5 µL | 2.5 µL | 2.5 µL | 1× |
| IsoAmp Enzyme Mix II (BioHelix) | 2 µL | 2 µL | 2 µL | 2× |
| GspSSD (OptiGene, 8 U/µL) | 2 µL | 2 µL | 2 µL | 0.64 U/µL |
| MgSO$_4$ (100 mM) + H$_2$O | As listed in the table below | As listed in the table below | As listed in the table below | 6 mM, 7, 8, 9, or 10 mM |

| | 6 mM | 7 mM | 8 mM | 9 mM | 10 mM |
|---|---|---|---|---|---|
| MgSO$_4$ (100 mM) | 1.5 µL | 1.75 µL | 2 µL | 2.25 µL | 2.5 µL |
| dH$_2$O | 1 µL | 0.75 µL | 0.5 µL | 0.25 µL | 0 µL |

After each reaction was incubated at 65° C. for 90 min, sample (10 µL) was diluted with a solution of plus of loading dye (4 µL), and loaded on a 2.5% agarose gel. Electrophoresis was used to resolve the PCR products. The results are shown in FIG. 6.

EXAMPLE 4

Demonstrating the Functioning of SAMRS-substituted Primers in HDA-like Assays Targeting HIV Genes Using GsSSD DNA Polymerases Oligonucleotides used in amplifying HIV-DNA target are shown below. The underlined bold A indicates A* as 2-aminopurine; the underlined bold T indicates T* as 2-thio-T; the underlined bold G indicates G* as inosine; the underlined bold C indicates C* as N-ethyl-dC. All components (primers, substituted or standard, 2'-deoxynucleoside triphosphates, polymerases, and helicase as part of the IsoAmp kit, obtained from BioHelix), were mixed at room temperature. They were then incubated at 65° C. for 90 min as indicated in Table 4. Primers in this example were extended at their 5'-ends by four nucleotides (indicated by lower case letters):

5'. GagF_Std_30mer:
SEQ ID NO. 13
5'-aaacACCATGCTAAACACAGTGGGGGGACA-3'

6'. GagR_Std_31mer:
SEQ ID NO. 14
5'-atctATCCCATTCTGCAGCTTCCTCATTGAT-3'

5. GagF_SMS_30mer:
SEQ ID NO. 15
5'-aaacACCATGCTAAACACAGTGGGGGGACA-3'

6. GagR_SMS_31mer:
SEQ ID NO. 16
5'-atctATCCCATTCTGCAGCTTCCTCATTGAT-3'

TABLE 4

| Components | HIV-Std-Primers | HIV-SAMRS-Primers | No Template Control | Final Conc. |
|---|---|---|---|---|
| dH₂O in primer mix | 9 μL | 9 μL | 9 μL | 25 μL |
| 5'. GagF-Std-30mer (5 μM) | 1 μL | | 1 μL | 0.2 μM |
| 6'. GagR-Std-31mer (5 μM) | | | | 0.2 μM |
| 5. GagF-SMS-30mer (5 μM) | | 1 μL | 1 μL | 0.2 μM |
| 6. GagR-SMS-31mer (5 μM) | | | | 0.2 μM |
| dH₂O in negative control | | | 2 μL | |
| HIV-DNA-96mer (0.1 fmole/μL) | 2 μL | 2 μL | | 20 ng/25 μL |
| IsoAmp dNTP Solution | 2 μL | 2 μL | 2 μL | 1.14× |
| NaCl (500 mM) | 2 μL | 2 μL | 2 μL | 40 mM |
| 10× Annealing Buffer II | 2.5 μL | 2.5 μL | 2.5 μL | 1× |
| IsoAmp Enzyme Mix II (BioHelix) | 2 μL | 2 μL | 2 μL | 2× |
| GspSSD (OptiGene, 8 U/μL) | 2 μL | 2 μL | 2 μL | 0.64 U/μL |
| MgSO₄ (100 mM) + H₂O | As listed in the table below | As listed in the table below | As listed in the table below | 6 mM, 7, 8, 9, or 10 mM |

| | 6 mM | 7 mM | 8 mM | 9 mM | 10 mM | Final Mg²⁺ (mM) |
|---|---|---|---|---|---|---|
| MgSO₄ (100 mM) | 1.5 μL | 1.75 μL | 2 μL | 2.25 μL | 2.5 μL | |
| dH₂O | 1 μL | 0.75 μL | 0.5 μL | 0.25 μL | 0 μL | |

After each reaction was incubated at 65° C. for 90 min, sample (10 μL) was diluted with a solution of plus of loading dye (4 μL), and loaded on a 2.5% agarose gel. Electrophoresis was used to resolve the PCR products. The results are shown in FIG. 7.

---

What is claimed is:

1. A process for synthesizing a preselected target DNA molecule, where said target DNA molecule binds to a complementary DNA molecule to form a duplex, said process comprising contacting said duplex in buffered aqueous solution with a helicase, a DNA polymerase, a single strand binding protein, 2'-deoxynucleoside triphosphates, and a substituted primer, said substituted primer that is complementary in sequence to a segment within said target DNA molecule, and where within said substituted primer one adenine in at least one of its 2'-deoxyadenosine nucleotides is substituted by 2-aminopurine or diaminopurine, or one guanine in at least one of its 2'-deoxyguanosine nucleotides is substituted by inosine, or one thymine in at least one of its thymidine nucleotides is substituted by 2-thiothymine, or at least one cytosine in at least one of its 2'-deoxycytidine nucleotides is substituted N4-ethylcytosine, and wherein the total number of said substitutions is between two and six, wherein said polymerase is Bst 2.0, GspSSD, GspM, or GspM2.0.

2. An amplification process for creating multiple copies of a target DNA molecule, said process comprising contacting said duplex in buffered aqueous solution with a helicase, a DNA polymerase, a single strand binding protein, 2'-deoxynucleoside triphosphates, and two substituted primers, a forward primer and a reverse primer, said forward primer binding to a segment within said target DNA molecule, and said reverse primer being substantially identical in sequence to a segment downstream within said target DNA molecule, and where within both of said substituted primers one adenine in at least one of its 2'-deoxyadenosine nucleotides is substituted by 2-aminopurine or diaminopurine, or one guanine in at least one of its 2'-deoxyguanosine nucleotides is substituted by inosine, or one thymine in at least one of its thymidine nucleotides is substituted by 2-thiothymine, or at least one cytosine in at least one of its 2'-deoxycytidine nucleotides is substituted by N4-ethylcytosine, and wherein the total number of said substitutions is between two and six, wherein said polymerase is Bst 2.0, GspSSD, GspM, or GspM2.0.

3. The process of claim 1 wherein appended to the 5'-end one or more of said substituted primers is a tag that comprises a preselected oligonucleotide that contains at least one nucleotide selected from the group consisting of

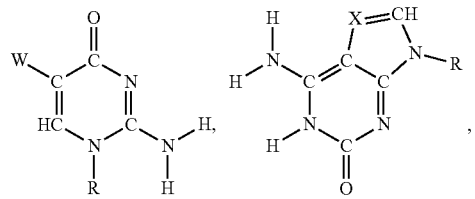

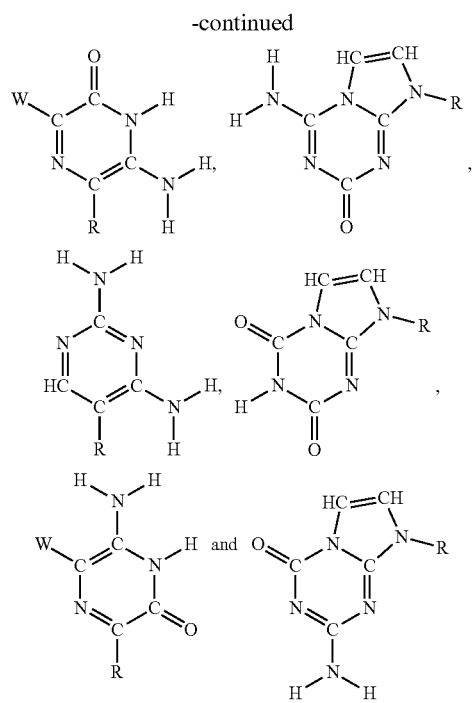

wherein X is selected from the group consisting of N and CH, W is nitro, cyano, or another electron withdrawing group, and R is the point of attachment of the indicated heterocycle to the oligonucleotide.

4. The process of claim 2 wherein appended to the 5'-end one or more of said substituted primers is a tag that comprises a preselected oligonucleotide that contains at least one nucleotide selected from the group consisting of

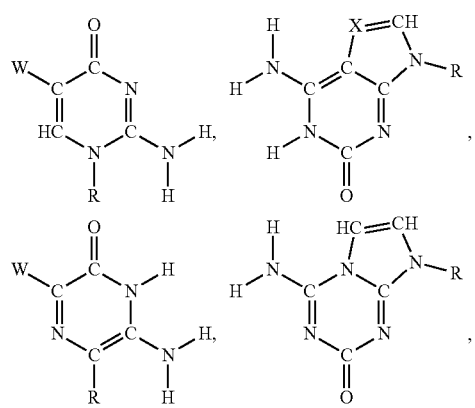

-continued

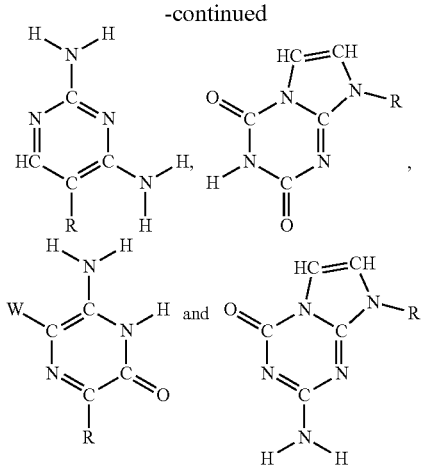

wherein X is selected from the group consisting of N and CH, W is nitro, cyano, or another electron withdrawing group, and R is the point of attachment of the indicated heterocycle to the oligonucleotide.

5. The process of claim 1, wherein said substitutions are placed in the 3'-terminal seven sites of said primer.

6. The process of claim 2, wherein said substitutions are placed in the 3'-terminal seven sites of said primers.

7. The process of claim 1, wherein the total number of said substitutions is four, and these are placed in the 3'-terminal five sites of said primer.

8. The process of claim 2, wherein the total number of said substitutions is four, and these are placed in the 3'-terminal five sites of said primers.

* * * * *